United States Patent
Doney

(10) Patent No.: US 8,613,946 B2
(45) Date of Patent: Dec. 24, 2013

(54) CAROTENOIDS OF ENHANCED BIOAVAILABILITY

(75) Inventor: John A. Doney, Washington, DC (US)

(73) Assignee: ISP Investment Inc., Wilmington, DE (US)

( * ) Notice: Subject to any disclaimer, the term of this patent is extended or adjusted under 35 U.S.C. 154(b) by 936 days.

(21) Appl. No.: 11/962,311

(22) Filed: Dec. 21, 2007

(65) Prior Publication Data

US 2008/0181960 A1     Jul. 31, 2008

Related U.S. Application Data

(60) Provisional application No. 60/876,805, filed on Dec. 21, 2006.

(51) Int. Cl.
| | |
|---|---|
| A61K 9/20 | (2006.01) |
| A61K 9/14 | (2006.01) |
| A61K 47/00 | (2006.01) |
| A61K 31/045 | (2006.01) |

(52) U.S. Cl.
USPC ............ 424/464; 424/489; 514/781; 514/729

(58) Field of Classification Search
USPC ........................ 424/464, 489; 514/781, 729
See application file for complete search history.

(56) References Cited

U.S. PATENT DOCUMENTS

| | | | |
|---|---|---|---|
| 2,861,891 A * | 11/1958 | Bauernfeind et al. | 426/540 |
| 3,981,676 A | 9/1976 | Ghilardi et al. | |
| 4,572,915 A | 2/1986 | Crooks | |
| 4,826,689 A | 5/1989 | Violanto et al. | |
| 4,956,386 A | 9/1990 | McLoughlin et al. | |
| 5,340,591 A | 8/1994 | Nakano et al. | |
| 5,443,842 A | 8/1995 | Seghizzi et al. | |
| 5,460,823 A * | 10/1995 | Jensen et al. | 424/451 |
| 5,519,021 A | 5/1996 | Young et al. | |
| 5,663,169 A | 9/1997 | Young et al. | |
| 5,665,720 A | 9/1997 | Young et al. | |

(Continued)

FOREIGN PATENT DOCUMENTS

| | | |
|---|---|---|
| EP | 1249232 | 10/2002 |
| EP | 1932520 | 6/2008 |

(Continued)

OTHER PUBLICATIONS

PCT, International Search Report, PCT/US2007/088501 (Oct. 10, 2008).

(Continued)

*Primary Examiner* — Aradhana Sasan
(74) *Attorney, Agent, or Firm* — Thompson Hine LLP; William J. Davis

(57) ABSTRACT

Carotenoid compositions of enhanced solubility and bioavailability are described that contain at least one carotenoid with at least one solubility-enhancing polymer. In one embodiment, the carotenoid is a provitamin A carotenoid such as β-carotene. In another embodiment the carotenoid is a non-provitamin A carotenoid such as lycopene or lutein. Described methods to produce the bioenhanced products include dry blending and solvent spray drying. In accordance with certain embodiments of the invention, the method includes the steps of providing a mixture comprising the carotenoid, a solubility-enhancing polymer and a solvent and removing the solvent to produce an amorphous form of the carotenoid. Products made by the invention's compositions and methods include pharmaceuticals, nutraceuticals, cosmetic, and personal care products for man and animal.

12 Claims, 1 Drawing Sheet

(56) References Cited

U.S. PATENT DOCUMENTS

| | | | |
|---|---|---|---|
| 5,811,423 A | 9/1998 | Young et al. | |
| 5,811,609 A * | 9/1998 | Vilstrup et al. | 585/351 |
| 5,863,953 A | 1/1999 | Lüddecke et al. | |
| 5,871,775 A | 2/1999 | Valducci | |
| 5,968,251 A * | 10/1999 | Auweter et al. | 106/498 |
| 5,989,583 A | 11/1999 | Amselem | |
| 6,056,971 A | 5/2000 | Goldman | |
| 6,143,211 A | 11/2000 | Mathiowitz et al. | |
| 6,184,255 B1 | 2/2001 | Mae et al. | |
| 6,197,349 B1 | 3/2001 | Westesen et al. | |
| 6,221,398 B1 | 4/2001 | Jakupovic et al. | |
| 6,300,377 B1 | 10/2001 | Chopra | |
| 6,403,116 B1 | 6/2002 | Anderson et al. | |
| 6,462,093 B1 | 10/2002 | Miyamoto et al. | |
| 6,548,555 B1 | 4/2003 | Curatolo et al. | |
| 6,555,133 B2 | 4/2003 | Makooi-Morehead et al. | |
| 6,579,521 B2 | 6/2003 | Sahner | |
| 6,582,729 B1 | 6/2003 | Eljamal et al. | |
| 6,689,755 B1 | 2/2004 | Gabel et al. | |
| 6,723,359 B2 | 4/2004 | Subramaniam et al. | |
| 6,740,338 B1 | 5/2004 | Chopra | |
| 6,746,635 B2 | 6/2004 | Mathiowitz et al. | |
| 6,763,607 B2 | 7/2004 | Beyerinck et al. | |
| 6,923,988 B2 | 8/2005 | Patel et al. | |
| 6,973,741 B2 | 12/2005 | Beyerinck et al. | |
| 7,109,361 B2 | 9/2006 | Hoffman et al. | |
| 2002/0006443 A1 | 1/2002 | Curatolo et al. | |
| 2002/0009494 A1 | 1/2002 | Curatolo et al. | |
| 2002/0043571 A1* | 4/2002 | Nowotny et al. | 239/225.1 |
| 2003/0049321 A1 | 3/2003 | Begon et al. | |
| 2003/0091643 A1 | 5/2003 | Friesen et al. | |
| 2003/0104063 A1 | 6/2003 | Babcock et al. | |
| 2003/0147965 A1 | 8/2003 | Bassett et al. | |
| 2003/0157182 A1 | 8/2003 | Staniforth et al. | |
| 2003/0170309 A1 | 9/2003 | Babcock et al. | |
| 2003/0224043 A1 | 12/2003 | Appel et al. | |
| 2004/0013734 A1 | 1/2004 | Babcock et al. | |
| 2004/0175428 A1 | 9/2004 | Appel et al. | |
| 2004/0194338 A1 | 10/2004 | Beyerinck et al. | |
| 2005/0002870 A1 | 1/2005 | Osborne | |
| 2005/0031692 A1 | 2/2005 | Beyerinck et al. | |
| 2005/0049223 A1 | 3/2005 | Curatolo et al. | |
| 2005/0079138 A1 | 4/2005 | Chickering, III et al. | |
| 2005/0133949 A1 | 6/2005 | Stoy | |
| 2005/0139144 A1 | 6/2005 | Muller et al. | |
| 2005/0143404 A1 | 6/2005 | Rosenberg et al. | |
| 2005/0169988 A1 | 8/2005 | Tao et al. | |
| 2005/0169999 A1* | 8/2005 | Eller et al. | 424/489 |
| 2005/0170000 A1 | 8/2005 | Walker et al. | |
| 2005/0170002 A1 | 8/2005 | Kipp et al. | |
| 2005/0226858 A1 | 10/2005 | Kitamura et al. | |
| 2008/0248117 A1* | 10/2008 | Kolter et al. | 424/486 |

FOREIGN PATENT DOCUMENTS

| | | | |
|---|---|---|---|
| GB | 988122 | 4/1965 | |
| GB | 1201171 | 8/1970 | |
| GB | 2401547 | 11/2004 | |
| WO | 97/13503 | 4/1997 | |
| WO | 97/36577 | 10/1997 | |
| WO | WO 99/42134 * | 8/1999 | A61K 47/00 |
| WO | 00/40220 | 7/2000 | |
| WO | 03/045327 | 6/2003 | |
| WO | 03/049701 | 6/2003 | |
| WO | 03/063821 | 8/2003 | |
| WO | 03/068008 | 8/2003 | |
| WO | 2004/080933 | 9/2004 | |
| WO | 2004/098570 | 11/2004 | |
| WO | 2005/000267 | 1/2005 | |
| WO | 2005/041929 | 5/2005 | |
| WO | 2005/087208 | 9/2005 | |
| WO | 2006/033734 | 3/2006 | |
| WO | 2006/053379 | 5/2006 | |
| WO | 2006/082500 | 8/2006 | |
| WO | 2006/134610 | 12/2006 | |
| WO | WO 2006/131481 A1 * | 12/2006 | A61K 9/14 |

OTHER PUBLICATIONS

Chew, N.Y.K. et al., "Use of Solid Corrugated Particles to Enhance Powder Aerosol Performance," Pharmaceutical Research, vol. 18, No. 11, pp. 1570-1577 (Nov. 2001).

Bain, D.F. et al., "Solvent Influence on Spray-Dried Biodegradable Microspheres," J. Microencapsulation, vol. 16, No. 4, pp. 453-474 (1999).

Raula, J. et al., "Influence of the Solvent Composition on the Aerosol Synthesis of Pharmaceutical Polymer Nanoparticles," International Journal of Pharmaceutics, 284, pp. 13-21 (2004).

Hancock, B.C. et al., "Molecular Mobility of Amorphous Pharmaceutical Solids Below Their Glass Transition Temperatures," Pharmaceutical Research, vol. 12, No. 6, pp. 799-806 (1995).

Maa, Yuh-Fun et al., "The Effect of Operating and Formulation Variables on the Morphology of Spray-Dried Protein Particles," Pharmaceutical Development and Technology, 2(3), pp. 213-223 (1997).

Matsuda, Y. et al., "Improvement of the photostability of ubidecarenone microcapsules by incorporating fat-soluble vitamins," International Journal of Pharmaceutics 1985 Netherlands, vol. 26, No. 3, pp. 289-301 (1985).

PCT, International Search Report issued regarding International Application No. PCT/US2006/029821 (published Jun. 21, 2007).

PCT, International Search Report issued regarding International Application No. PCT/US2006/029822 (published May 31, 2007).

PCT, International Search Report issued regarding International Application No. PCT/US2006/029604 (published Feb. 14, 2008).

PCT, International Preliminary Report on Patentability issued regarding International Application No. PCT/US2006/029822 (dated Jan. 29, 2008).

PCT, International Preliminary Report on Patentability issued regarding International Application No. PCT/US2006/029821 (dated Jan. 29, 2008).

PCT, International Preliminary Report on Patentability issued regarding International Application No. PCT/US2006/029604 (dated Jan. 29, 2008).

XP0024247891 Database CA [Online] Chemical Abstracts Service, Columbus, Ohio, US "Pharmaceuticals containing ubidecarenone at high concentrations and effective dispersing agents" retrieved from STN, Feb. 14, 1985.

* cited by examiner

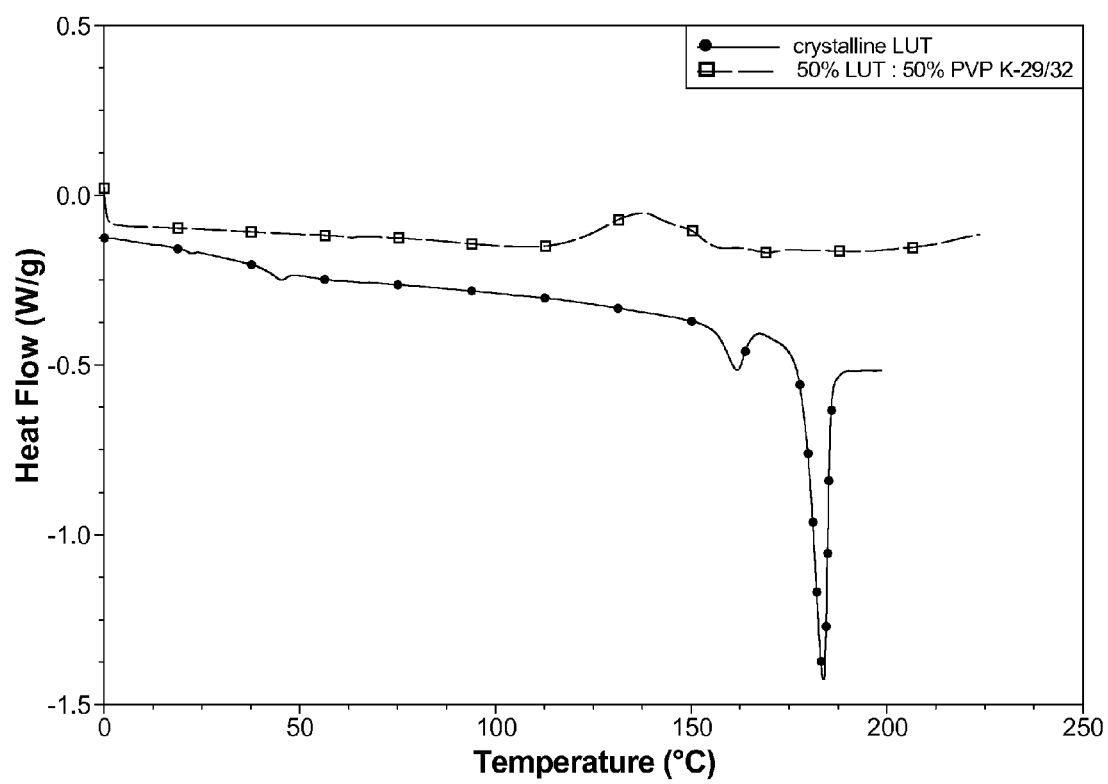

CAROTENOIDS OF ENHANCED BIOAVAILABILITY

CROSS REFERENCE TO RELATED APPLICATION

This application claims the benefit of U.S. Provisional Application Ser. No. 60/876,805, filed Dec. 21, 2006, the contents of which are hereby incorporated by reference.

BACKGROUND OF THE INVENTION

Carotenoids are naturally occurring red, yellow, orange, and green pigments produced by plants and some types of fungi and bacteria. It is believed that these pigments help protect the organism from potentially damaging effects of oxygen and light. Carotenoid molecules typically possess a series of conjugated double bonds, and can be divided into two groups. The provitamin A family of carotenoids, which are synthesized by the body to vitamin A, includes α- and β-carotene, and β-cryptoxanthin. Carotenoids that are not precursors to vitamin A include lycopene, lutein, and zeaxanthin. Studies suggest carotenoids offer anti-carcinogenic and anti-atherogenic protection.

As a family, carotenoids generally exhibit poor water solubility and low absorption from the gastrointestinal tract. The Merck Index, the relevant portions of which are hereby incorporated by reference, classifies α- and β-carotene, and zeaxanthin as "practically insoluble in water," while lutein (also known as xanthophyll) is "insoluble in water." The *PDR For Nutritional Supplements*, the relevant portions of which are hereby incorporated by reference, states that lycopene is "insoluble in water." As a result of their poor water solubility, carotenoids also exhibit low bioavailability. For example, a study by Diwadkar-Navsariwala et al. (2003), which is incorporated by reference, reported that human lycopene absorption is poor and relatively constant, ranging between 3.4 mg-6.4 mg, even for escalating lycopene doses ranging from 10 mg-120 mg. Thus, there exists the need to enhance the bioavailability of carotenoids.

In addition to poor solubility, carotenoids also exhibit poor stability. In particular, the conjugated double bond structure of carotenoids renders them particularly susceptible to oxidation and light-induced degradation. Formulation techniques such as the use of protective colloids or emulsification systems have been used to prevent carotenoid degradation, but these techniques typically result in low active loads and/or limit final dosage formulation flexibility.

Carotenoids are well known in the dietary supplement market, primarily in two dosage forms: softgels and tablets. Softgel dosage forms typically contain beeswax, lecithin, gelatin, edible oils, glycerin and/or other emulsification technology to enhance the solubility of the carotenoid. However, soft gel technology is a more labor- and cost-intensive process than capsule/tablet technologies. Furthermore, emulsified carotenoid compositions are not well-suited for formulating with non-emulsified ingredients. Tablet forms of the carotenoids typically contain excipients such as microcrystalline cellulose, croscarmellose sodium, titanium dioxide, silicon dioxide and magnesium stearate to assist tableting, which may not provide bioenhancement or stability of the carotenoid.

U.S. Pat. No. 5,968,251 discloses a process to produce carotenoid compositions whereby an organic, water-miscible solution is first prepared containing a carotenoid colloid, which is then transferred into an aqueous phase to remove the organic solvent, leaving a nanodispersed carotenoid phase.

U.S. Pat. No. 5,863,953 discloses a double dispersion system in which particles are stabilized by a protective colloid dispersed in edible oil as a dispersion medium.

It is desirable to produce solid compositions of carotenoids exhibiting enhanced solubility and/or bioavailability and/or stability compared to the crystalline form of the compound. By converting a substantial portion of a crystalline carotenoid to the amorphous state, the aqueous solubility and bioavailability are increased. Furthermore, by incorporating the carotenoid in a solid dispersion, it may be protected from oxidation or light induced degradation. In addition, carotenoids presented as an amorphous solid may facilitate manufacturing of the finished product and provide dosage forms that are substantially free of added lipids or oils or that may contain other active ingredients.

Accordingly, certain embodiments of the present invention provide one or more of the following benefits:
1. Enhanced solubility and bioavailability of carotenoids;
2. Enhanced stability of carotenoids;
3. An enhanced form of carotenoids that does not require the use of oils, gelatins, or emulsification technology to allow for the preparation of capsules/tablets;
4. Increased flexibility in formulation and final product performance (i.e., release rate, powder compactability, multiple actives);
5. A more cost-effective method for providing this enhancement than technologies currently employed for preparing bioenhanced or stabilized carotenoids (e.g., softgel capsules, colloidal dispersions, emulsification technologies).

Thus, in accordance with certain embodiments, the present invention relates to compositions of stable and/or bioenhanced carotenoids and methods for producing them. More particularly, certain aspects of the present invention relate to compositions and methods for preparing stable and/or bioenhanced carotenoids utilizing at least one solubility-enhancing organic material. In a preferred embodiment of the invention, the solubility-enhancing organic material is a polymer. In accordance with certain embodiments, the carotenoid is a provitamin A carotenoid (e.g., α-carotene, β-carotene, or β-cryptoxanthin) or a non-provitamin A carotenoid (e.g., lycopene, lutein, or zeaxanthin). Mixtures of carotenoids or a carotenoid with other actives are within the scope of the invention.

In one embodiment, the mixture is prepared by dry blending the carotenoid with a solubility-enhancing polymer. In another embodiment, the carotenoid is dissolved in a solvent containing the polymer. In yet another embodiment, a blend of solvent/non-solvent for the polymer is employed. The stable and/or bioenhanced carotenoid product is produced by any method suitable to the composition. In one embodiment, direct compression of physically blended carotenoid(s)-polymer(s) is used. When necessary, solvent can be removed from compositions to yield the stable and/or bioenhanced carotenoid product. In one further development of the invention, a carotenoid-polymer-solvent (or a solvent/non-solvent blend) solution or dispersion is spray dried to produce the carotenoid in a form that exhibits improved stability, solubility and/or bioavailability. The stable and/or bioenhanced carotenoid composition can be prepared by methods other than spray drying as recognized by those skilled in the art. Those methods include, without limitation: melt extrusion, spray congealing, and freeze drying. In accordance with particular embodiments of the invention, a significant portion of the carotenoid is provided in the amorphous state. In accordance with certain embodiments, the carotenoid is converted almost entirely to the amorphous state. In one embodiment of the invention, the carotenoid is converted to the completely amorphous state.

SUMMARY OF THE INVENTION

In accordance with particular embodiments of the present invention, compositions are described containing carotenoids and methods are provided for producing carotenoid compositions of enhanced stability, solubility and/or bioavailability. Mixtures of carotenoids and solubility-enhancing polymers show enhanced aqueous stability and/or solubility compared to the crystalline form. Examples of compositions that may create this enhancement include, without restriction: solid dispersions and physical blends of the components. Surprisingly, simple dry mixtures of a carotenoid and polymer may attain dissolution release characteristics equal to many commercial softgel carotenoid products, which employ lipids, oils and/or triglycerides. Even faster release with greater extent is produced with amorphous carotenoid-polymer dispersions, as shown in several embodiments of the invention.

Although preferable, the amorphous conversion of the carotenoid is not a requirement for the enhanced properties. A composition comprising a solid dispersion of a carotenoid and at least one solubility-enhancing polymer wherein the carotenoid in the dispersion is substantially amorphous is also provided. In one aspect, the disclosed invention describes the conversion of crystalline carotenoid to the amorphous state. One method for producing this conversion is through solvent spray drying. Other techniques within the scope of this invention that accomplish this conversion include, without limitation: flash solvent evaporation, melt-congeal spraying, freeze drying, and melt-extrusion. These methods can use a single solubility-enhancing polymer or blends of polymers. Accordingly, products can be developed that serve the vegan/all natural market (e.g., using naturally-occurring ingredients/adjuvants) and a broader market (e.g., using synthetic ingredients/adjuvants). The degree of carotenoid amorphous conversion depends on both polymer type and amount and processing conditions. When required, a single organic solvent, blends of solvents, or solvent/non-solvent blends can be used.

By converting a substantial portion of crystalline carotenoid to the amorphous form, its aqueous solubility is increased, which, in turn, improves its bioavailability. In one embodiment, a solution is prepared comprising a solvent, one or more carotenoids, and one or more solubility-enhancing organic materials. The choice of solvent is only limited inasmuch as to produce a carotenoid solution, and examples of suitable solvents include dichloromethane/methanol blends, and chloroform. The solvent may dissolve both the carotenoid and solubility-enhancing organic material, or a non-solvent for the organic material optionally may be added. In a preferred embodiment, the solubility-enhancing organic material comprises a polymer. In another preferred embodiment, the solubility-enhancing organic material comprises a carbohydrate. The organic material may be of any type approved for use in pharmaceutical and/or dietary supplement products.

In one aspect, the invention relates to spray-dried powders or granulated products comprising an amorphous carotenoid. In addition, the resulting powders produced in accordance with certain embodiments typically possess lower residual solvent content and higher tap density than their counterparts produced by conventional methods, due to a change in the particle morphology and size.

One aspect of the invention involves amorphous carotenoids prepared from compositions containing a carotenoid and a solubility-enhancing organic material in a solvent or a solvent blend. This solvent or solvent blend includes a solvent in which the solubility-enhancing organic material is soluble. In a preferred embodiment, the solubility-enhancing organic material is a polymer. The term "soluble" means that the attractive force between polymer and solvent molecules is greater than the competing inter- and intramolecular attractive forces between polymer molecules. For simplicity, this solvent is simply called "solvent." Compositions also are described in which the solvent blend contains a solvent for which the opposite is true: The force between polymer and solvent molecules is less than the inter- and intramolecular attractive force between polymer molecules. This second solvent is termed the "non-solvent." The polymer may swell but does not dissolve in the non-solvent. In accordance with one embodiment of the invention, a solubility-enhancing polymer and a suitable solvent/non-solvent blend are provided. Additionally, the solvent possesses a lower boiling point than the non-solvent. Preferably, the solvent and non-solvent are miscible. The ratio of solvent to non-solvent is such that the polymer can be considered "dissolved" in the solvent system.

Unique particle properties can be created by evaporating the solvent/non-solvent blend. For example, this evaporation can occur during the spray drying of the feed solution or granulation processes. Atomized droplets containing a blend of solvents will experience a change in the total solvent composition due to evaporation. The method appears to be independent of how the droplets are generated or atomized. Initially, the polymer exists in a dissolved state, due to a sufficient amount of the solvent. As it evaporates (the solvent boils at a lower temperature than the non-solvent), the concentration of non-solvent in the droplet increases. Eventually, the solvent composition is insufficient to maintain the polymer in solution. In doing so, the polymer collapses from solution. This change in polymer conformation can alter the evaporation dynamics of the droplet to create particle morphologies that influence final powder properties.

Although carotenoids of enhanced solubility and bioavailability can be formed by spray drying from a solution containing solvent alone, there are additional benefits associated with the use of a solvent/non-solvent blend system. This solvent/non-solvent approach can produce a spray dried powder of lower residual solvent content and smaller particle size. A further consequence of this engineered particle morphology is the increase in bulk powder density. Increased powder density is an important attribute for many applications. The extent of polymer collapse—and therefore the net effect on the spray dried powder properties—depends on the polymer salvation factors, such as the initial ratio of solvent to non-solvent, the polymer chemical structure and the polymer molecular weight. In addition to reducing residual solvent content and increasing density, the primary polymer may be paired with the solvent/non-solvent system in order to affect not only the morphology of the particle, but also that of the carotenoid, and thereby affect active loading, crystallinity, solubility, stability and release.

The presence of additional polymers may contribute to the final particle morphology by their interaction with the first polymer and the solvent system. These additional polymers may also be advantageous to create special release properties of the active. For example, the primary polymer may be paired with the solvent/non-solvent system in order to affect particle morphology, and thereby residual solvent content and bulk powder density. Additional polymeric adjuvants may be added to serve additional purposes: further inhibit active recrystallization, further maximize active concentration, and further enhance/delay/retard dissolution rate. To accomplish these functionalities, it is necessary to suitably match the adjuvant solubilities with the solvent blend selected for the primary polymer.

BRIEF DESCRIPTION OF THE DRAWING

The FIGURE is a plot of heat flow vs. temperature for compositions produced in accordance with Example 1.

DETAILED DESCRIPTION OF THE INVENTION

The term "comprising" encompasses the more restrictive terms "consisting essentially of" and "consisting of."

All percentages, ratios and proportions used herein are by weight unless otherwise specified.

Bioavailability refers to the degree to which the active or active metabolite becomes available in the body after administration. Typically, plasma samples are taken and analyzed for the plasma concentration of the parent compound and/or its active metabolite. These data may be expressed as $C_{max}$, the maximum amount of active ingredient found in the plasma, or as AUC, the area under the plasma concentration time curve. Enhanced bioavailability may be evidenced by an increase in $C_{max}$ and/or AUC for the active, the active metabolite or both. Compositions in accordance with certain aspects of the invention exhibit enhanced bioavailability compared to a control composition.

The term "solid dispersion" as used herein refers to a system in a solid state comprising at least two components, wherein one component is dispersed evenly throughout the other component or components. The term "solid dispersion" includes systems having small particles either completely crystalline, completely amorphous or any state in between, typically less than about 1 μm in diameter, of one phase dispersed in another phase.

The term "solid solution" as used herein refers to a type of solid dispersion wherein one component is molecularly dispersed throughout another component such that the system is chemically and physically uniform and homogeneous throughout. These systems do not contain any significant amounts of active ingredients in their crystalline or microcrystalline state as evidenced by thermal analysis (e.g., differential scanning calorimetry), or diffractive (e.g., X-ray diffraction) techniques.

The term "solubility-enhancing polymer" refers to a polymer that provides at least one of the following properties as a result of its presence in the composition compared to a control composition without the solubility-enhancing polymer:
 a) an increase in initial release of at least about 25%
 b) an increase in extent of release of at least about 25%
 c) an increase in maximum plasma concentration of at least about 25%
 d) an increase in $AUC_{0-24h}$ of at least about 25%.

There is no condition placed on the state of the compositions other than one or more carotenoid(s) is combined with one or more solubility-enhancing organic material(s). The term "combined" includes, but is not limited to: blended, co-mingled, dissolved, extruded, granulated, melted, milled, mixed, sieved, slurried, sprayed, stirred, and the combination of these and other methods. Other techniques may be identified by those skilled in the art. Furthermore, compositions of the current invention may include additional active ingredients to the carotenoid(s). Active pharmaceutical ingredients include, but are not limited to: analgesics, anti-arrhythmics, anti-bacterials, anti-convulsants, anti-Alzheimer's agents, anti-diabetics, anti-emetics, anti-fungals, anti-histiminics, anti-hyperlipidemics, anti-hyperlipoproteinemics, anti-hypertensives, anti-inflamatory agents, anti-Parkinsonian agents, anti-pulmonary hypertensives, anti-rheumatics, anti-ulceratives, anti-virals, cardiovascular agents, chemotherapy agents, central nervous system sedatives and stimulants, diuretics, gastrointestinal agents, hormones, respiratory agents, skin agents, as well as actives for the treatment of acne, benign prostatic hypertrophy, irritable bowel syndrome. Nutraceutical ingredients include, but are not limited to: herbs, isoflavones, benzoquinones, moisturizers, mood regulators, minerals, oils, protein supplements, skin agents, ultraviolet blocking agents, and vitamins.

Although the following description is primarily directed to the preparation of a spray-dried composition containing lycopene, the present invention is not limited to lycopene spray-dried compositions. The methods described herein are also useful in converting other carotenoids such as β-carotene or lutein to the amorphous state of enhanced stability, solubility and/or bioavailability. Physical mixtures of a carotenoid and a solubility-enhancing polymer that increase the solubility and bioavailability of the carotenoid are also within the scope of the present invention. Physical mixtures can be prepared in accordance with conventional techniques such as a tumble blender, high-shear granulation, fluid bed granulation, film coating, or any of their related technologies.

In accordance with one embodiment, the present invention is related to a method for preparing a spray-dried composition by providing a mixture containing a carotenoid and a polymer in a single solvent, a solvent blend or a blend of a solvent and a non-solvent for the polymer and spray drying the mixture to form the amorphous carotenoid composition.

One aspect of the invention involves the pairing of the polymer with a carefully selected solvent or solvent blend. This approach comprises a solvent in which the polymer is soluble. Guidance in defining polymer solubility is provided by the expansion coefficient (α):

$$\alpha = \frac{(\overline{r^2})^{1/2}}{(\overline{r_o^2})^{1/2}} \tag{§1}$$

where $\overline{r^2}$ is the mean-square distance between chain ends, and $\overline{r_o^2}$ is the unperturbed dimension. (Equation §1 can be written for branched polymers in an analogous manner, using square-average radius of gyration about the center of gravity, $\overline{s^2}$, and the corresponding unperturbed dimension, $\overline{s_o^2}$.) Polymer solubility is provided when α is unity or greater, and solvents that satisfy this condition are called "good solvents," or simply "solvents." Solvents uncoil (or expand) the polymer molecule, since the polymer-solvent attractive force is greater than that of polymer-polymer. Light scattering methods, such as Viscotek's Triple Detector Array, can be used to determine the variables expressed in equation §1. These concepts are defined in the text *Polymer Chemistry, An Introduction*, by Malcolm P. Stevens, which is incorporated by reference.

When α equals unity, a special condition exists in that polymer-solvent and polymer-polymer forces are balanced. Solvents that enable this condition are called θ solvents. Within the context of this invention, solvents are considered "good solvents" when α is about equal to 1 or more. It is appreciated that temperature influences α, such that a good solvent may be transformed into a non-solvent merely by changing the temperature.

In yet another embodiment of this invention, the solvent blend also contains a solvent for which the opposite is true:

Polymer-polymer forces dominate polymer-solvent forces. In this case, α is less than one and the solvent is termed a "non-solvent," because the polymer exists in a collapsed state. In accordance with one embodiment of the invention, the polymer is provided in a suitable solvent/non-solvent blend. The blend of solvent/non-solvent maintains a θ or solvated state of the polymer, such that the polymer can be considered "dissolved" in the solvent system. Additionally, the solvent possesses a lower boiling point than the non-solvent. (Solvent/non-solvent pairs that form an azeotrope do not satisfy this criterion.)

In accordance with another aspect of the invention, a polymer system is provided comprising a solubility-enhancing polymer and a suitable solvent/non-solvent blend. Specific examples of suitable polymer/solvent/non-solvent combinations include, without limitation, polyvinylpyrrolidone/dichloromethane/acetone, polyvinylpyrrolidone-co-vinyl acetate/acetone/hexane, and ethylcellulose/acetone/water. Unique particle architectures are created by precipitation of the primary polymer when the non-solvent concentration exceeds a critical value. This critical ratio $R_c$ can be defined:

$$R_c = \frac{\text{mass nonsolvent}}{\text{mass solvent} + \text{nonsolvent}}, \quad (\S2)$$

which is the maximum fraction of the non-solvent before polymer precipitation occurs. The ratio $R_c$ for a given system can be determined experimentally by identifying the mass fractions of each component that produce a significant increase in solution turbidity. If an $R_c$ value can be identified for a polymer system, then the system comprises a solvent/non-solvent blend. One example is a solution containing about 10% (w/w) polyvinylpyrrolidone, 18% (w/w) dichloromethane, and 72% (w/w) acetone, for which $R_c$ equals 0.80. Polymer systems typically will be used at solvent/non-solvent blends that are at or below the $R_c$ value for the system. It may be advantageous to formulate more complex polymer/solvent systems in order to control particle morphology/size as well as the crystallinity, solubility, bioavailability and release characteristics of the carotenoid.

The present invention in accordance with other embodiments provides a method to increase the density of spray-dried powders. Typically, spray drying produces sphere-like particles with some degree of interior void. This void increases particle bulk without mass and creates low-density material. Adding a non-solvent to the working solution/dispersion changes the particle size and morphology, leading to an increase in density. Particles may be smaller, wrinkled, dimpled, and/or collapsed compared to those prepared using only solvent. The solvent/non-solvent approach also reduces the mean particle size, allowing the powder to pack better. In addition, powder flow and powder-powder mixing properties are enhanced.

The present invention in accordance with certain aspects provides a method to reduce or eliminate the need for secondary drying of spray-dried powders and granulated materials. These products often contain residual solvent, and it is desirable or necessary to produce a drier product. A high residual solvent content can result from formulation or processing limitations. The general practice has been to use a solvent that dissolves the solids being spray dried. In doing so, solvent can be trapped inside the spray dried powder or granulated bead due to case hardening. The intentional pairing of a lower-boiling solvent with a higher-boiling non-solvent for the materials being processed can yield products of lower residual solvent due to the effect(s) of the non-solvent on the process polymers.

The present invention may further provide a method to enhance the aqueous solubility and modify the release of the carotenoid through selection of a polymer system with the solvent or solvent/non-solvent blend. The polymer system is chosen so that one (or more) polymer(s) work with the solvent/non-solvents to create novel particle morphologies. Additional polymer(s) may be added as needed to affect the solubility and release properties of the carotenoid, as well as particle morphology. Enhanced solubility can be achieved by a number of factors, including (but not limited to): improved wettability, creation of amorphous carotenoid forms, stabilization against recrystallization, and/or co-solvation effects. In doing so, a supersaturated solution of the carotenoid is produced. "Modified release" refers to changing the time frame in which the active is released, i.e., immediate, delay, extended. These modified releases are created by matching functional polymer(s) with the appropriate solvent/non-solvent blend.

Solvents and non-solvents suitable for use in the process of the present invention can be any organic compound (including water) in which the primary polymer is soluble in the case of solvents, or insoluble in the case of non-solvents. The choice and ratio of solvent/non-solvent depends on the choice of the primary polymer. Accordingly, the identification of an organic compound as a solvent or non-solvent depends on the primary polymer. Therefore, a solvent in one system may be a non-solvent in another. Particularly useful solvents and non-solvents include, but are not limited to: acetic acid, acetone, acetonitrile, anisole, 1-butanol, 2-butanol, butyl acetate, tert-butylmethyl ether, chlorobenzene, chloroform, cumene, cyclohexane, 1-2-dichloroethane, dichloromethane, 1-2-dimethoxyethane, N—N-dimethylacetamide, N—N-dimethylformamide, 1-4-dioxane, ethanol, 2-ethoxyethanol, ethyl acetate, ethylene glycol, ethyl ether, ethyl formate, formamide, formic acid, heptane, hexane, isobutyl acetate, isopropyl acetate, methanol, methyl acetate, 2-methoxyethanol, 3-methyl-1-butanol, methylbutylketone, methylcyclohexane, methylethyl ketone, methylisobutyl ketone, 2-methyl-1-propanol, N-methylpyrolidone, nitromethane, pentane, 1-pentanol, 1-propanol, 2-propanol, propyl acetate, pyridine, sulfolane, tetrahydrofuran, tetralin, 1-2-2-trichloroethene, toluene, water, and xylene. Mixtures of solvents and mixtures of non-solvents can also be used. In accordance with particular embodiments, solvent blends at the azeotropic composition (which boil at one common temperature) can comprise either the solvent or non-solvent, but not the solvent/non-solvent blend.

Solubility-enhancing polymers that are suitable for use in the mixtures of the present invention enhance the solubility of the carotenoid. In accordance with particular aspects of the present inventions, the solubility-enhancing polymer also inhibits crystallization of the carotenoid and, therefore, the presence of the polymer results in conversion of at least some of the crystalline carotenoid to the amorphous state. In accordance with those embodiments wherein a solvent/non-solvent blend is used, at least one polymer should be soluble in the solvent and not soluble in the non-solvent. Specific examples of useful polymers include, but are not limited to: aliphatic polyesters (e.g., poly D-lactide), carbohydrates (e.g., sucrose), carboxyalkylcelluloses (e.g., carboxymethylcellulose), alkylcelluloses (e.g., ethylcellulose), gelatins, hydroxyalkylcelluloses (e.g., hydroxypropyl cellulose (HPC)), hydroxyalkylalkyl celluloses (e.g., hydroxypropylmethyl cellulose (HPMC)), hydroxyalkylalkylcellulose derivatives, polyamines (e.g., chitosan), polyethylene glycols (e.g., PEG 8000, PEG 20000), methacrylic acid polymers and copolymers (e.g., Eudragit® series of polymers of Rohm Pharma, GmbH), homo- and copolymers of N-vinyl pyrrolidone (e.g., polyvinylpyrrolidone, polyvinylpyrrolidone-co-vinyl acetate), homo- and copolymers of vinyllactam, polysaccharides (e.g., alginic acid), starch, poly glycols (e.g., propylene glycol, polyethylene glycol), polyvinyl esters (e.g., polyvinyl acetate), and refined/modified shellac. The term "hydroxyalkylalkylcellulose derivatives" is meant to comprise hydroxypropylmethyl cellulose phthalate, and hydroxypropylmethyl cellulose acetate succinate. The amount of the polymer present in the mixture may range from about 1% to about 95%, more particularly from about 5% to 90%, by weight of the mixture, and in accordance with certain embodiments from about 25% to 75% by weight. Blends of polymers may also be used.

The bioenhanced composition, which may comprise a spray-dried mixture, includes a carotenoid, such as lycopene, as an active ingredient. The mixture may contain from about 1% to about 95% active, more particularly from about 20% to about 80% active, depending on the desired dose of the active. The weight ratio of carotenoid to polymer typically will be from about 95% carotenoid:5% total polymer to about 5% carotenoid:95% total polymer, more particularly from about 70% carotenoid:30% total polymer to about 30% carotenoid:70% total polymer and in accordance with certain aspects from about 60% carotenoid:40% total polymer to about 40% carotenoid:60% total polymer.

The spray dried composition of the present invention when combined with a solubility enhancing polymer produces a portion of the carotenoid in the amorphous state. The term "amorphous" refers to a compound in a non-crystalline state. In other words, an amorphous compound lacks long-ranged, defined crystalline structure. In accordance with certain embodiments of the present invention, at least some, more particularly at least about 10%, at least about 25%, or at least about 40% of the carotenoid in the composition is in an amorphous form. In other embodiments, at least a major portion of the compound in the composition is amorphous. As used herein, the term "a major portion" of the compound means that at least about 50% of the compound in the composition is in the amorphous form, rather than the crystalline form. More particularly, the compound in the composition may be substantially amorphous. As used herein, "substantially amorphous" means that the amount of the compound in the crystalline form does not exceed about 25% (i.e., more than about 75% of the compound is in the amorphous form). In accordance with particular embodiments of the invention, the compound in the composition is "almost completely amorphous" meaning that the amount of drug in the crystalline form does not exceed about 10% (i.e., more than about 90% of the compound is in the amorphous form). Compositions are also provided wherein the compound in the composition is considered to be "completely amorphous" meaning that the crystalline form of the drug is not detectable using conventional techniques, such as X-ray diffraction or thermal analysis. Reference to a composition as completely amorphous does not exclude compositions containing trace amounts (less than about 1%) of the crystalline form of the drug.

Amorphous materials lack some measurable properties, such as melting endotherms as measured by differential scanning calorimetry that characterize crystalline forms. Amounts of crystalline carotenoid may be measured by powder X-ray diffraction (PXRD), differential scanning calorimetry (DSC), or any other standard quantitative analysis. The amounts of crystalline carotenoid present in the composition may be detected by any other standard measurement known to those of ordinary skill in the art. It is appreciated that the measurement of such properties is dependent on instrument type, sensitivity, operation, and analysis.

By providing the carotenoid in the amorphous form, the spray dried powder produced in accordance with certain aspects of the present invention provides enhanced solubility and/or bioavailability of a carotenoid compared to products containing the principle crystalline form. The increased bioavailability of the active can also lead to reduced dosage sizes and dose amounts for the active. Applicants have also determined that the rate of carotenoid release can be controlled through proper selection of the polymers added into the solvent solution for the spray dried process.

The spray dried mixture or bioenhanced composition may also contain additional polymeric materials that can modify properties of the composition. For example, certain polymers can be included to control particle morphology/size as well as the solubility and bioavailability and release characteristics of the active ingredient. Additional polymers may also be included in the mixture to further inhibit active recrystallization, further maximize active concentration and further enhance/delay/retard dissolution rate. Additional polymers that can be incorporated into this system are not particularly limited.

The mixture to be spray dried typically contains from about 40% to 99.9% by weight total solvent or solvent/non-solvent, more particularly from about 80% to 95% by weight total solvent or solvent/non-solvent based on the total weight of the mixture. When a solvent/non-solvent blend is used, the critical ratio $R_c$ can vary from about 0.01-0.99, more particularly from about 0.1-0.9, still more particularly from about 0.3-0.8.

In addition to the solvent, polymer and carotenoid, the mixture to be spray dried may also include other ingredients to improve performance, handling or processing of the mixture. Alternatively, these ingredients also may be admixed into the already-prepared carotenoid-polymer by methods including, but not limited to tumble blending and granulation technologies. Typical ingredients include, but are not limited to, anti-oxidants, surfactants, pH modifiers, fillers, complexing agents, solubilizer, pigments, lubricants, glidants, flavor agents, plasticizers, taste masking agents, disintegrants, disintegrant aids (e.g., calcium silicates), etc. Examples of useful surfactants include, but are not limited to, sodium lauryl sulfate, docusate sodium, sorbitan monooleate, and sorbitan trioleate. Examples of useful fillers include, but are not limited to, lactoses, dextrin, sugars, sugar alcohols, and silica.

The spray drying apparatus used in accordance with certain aspects of the present invention can be any of the various commercially available apparatus or other devices capable of producing similar particles from liquid mixtures. Examples of specific spray drying devices include spray dryers manufactured by Niro Inc. (e.g., SD-Micro®, PSD-1®, PSD-2®, etc.), the Mini Spray Dryer® by Buchi Labortechnik AG, spray dryers manufactured by Spray Drying Systems, Inc. (e.g., models 30, 48, 72), and SSP Pvt. Ltd.

Spray drying processes and spray drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray drying processes and equipment are reviewed by Marshall "Atomization and Spray Drying," 50 *Chem. Eng. Prog. Monogr. Series* 2 (1954). The relevant contents of these references are hereby incorporated by reference.

The term "spray drying" is used conventionally and, in general, refers to processes involving breaking up liquid mixtures into small droplets and rapidly removing solvent from the mixture in a container (spray drying apparatus) where there is a strong driving force for evaporation of solvent from the droplets. Atomization techniques include two-fluid and pressure nozzles, and rotary atomizers. The strong driving force for solvent evaporation is generally provided by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas; or (3) both.

Generally, the temperature and flow rate of the drying gas and the design of the spray dryer are chosen so that the polymer/active solution droplets are dry enough by the time they reach the wall of the apparatus that they are essentially solid and so that they form a fine powder and do not stick to the apparatus wall. It is also possible to operate a spray dryer so that product collects on the apparatus wall, and then is collected by removing the material manually, pneumatically, mechanically or other means. The actual length of time to achieve the preferred level of dryness depends on the size of the droplets, the formulation, and spray dryer operation. Following the solidification, the solid powder may stay in the spray drying chamber for 5-60 seconds, further evaporating solvent from the solid powder. The final solvent content of the solid dispersion as it exits the dryer should be low, since this improves the stability of the product. Generally, the residual solvent content of the spray-dried composition should be less than about 10% by weight and preferably less than about 2% by weight. In accordance with certain embodiments, the residual solvent content is within the limits set forth in the International Conference on Harmonization (ICH) Guidelines. Although not typically required in accordance with certain aspects of the present invention, because the presence of a non-solvent produces a spray-dried powder of lower residual solvent content, it may be useful in accordance with certain embodiments of the present invention to subject the spray-dried composition to further drying to lower the residual solvent to even lower levels. Methods to further lower solvent levels include, but are not limited to fluid bed drying, infra-red drying, tumble drying, vacuum drying, and combinations of these and other processes. Additional detail with respect to a particular spray drying process is described in more detail in the examples. However, the operating conditions to spray dry a powder are well known in the art and can be easily adjusted by the skilled artisan. Furthermore, the examples describe results obtained with a laboratory-scale spray dryer. One of ordinary skill in the art would readily appreciate variables that must be modified to obtain similar results with a production-scale unit.

As indicated above, the present invention is not limited to an amorphous carotenoid produced by spray drying. Physical mixtures of a carotenoid with a solubility-enhancing polymer can also enhance the solubility and bioavailability of the carotenoid. Methods for preparing physical mixtures of the polymer and carotenoid are not particularly limited. In accordance with one aspect of the present invention, physical mixtures of solubility-enhancing polymer and carotenoid may be formed by tumble blending, co-milling, stirring, granulating, or other methods known to those skilled in the art.

In addition to spray drying, amorphous compositions of the present invention may be prepared by other processes including, but not limited to, extrusion, spheronization and spray congealing.

Extrusion is a well-known method of applying pressure to a damp or melted composition until it flows through an orifice or a defined opening. The extrudable length varies with the physical characteristics of the material to be extruded, the method of extrusion, and the process of manipulation of the particles after extrusion. Various types of extrusion devices can be employed, such as screw, sieve and basket, roll, and ram extruders.

In melt extrusion, components can be melted and extruded with a continuous process with or without a solvent and with or without inclusion of other additives. Such a process is well-established and well-known to skilled practitioners in the art.

Spheronization is the process of converting material into spheres, the shape with the lowest surface area to volume ratio. Spheronization typically begins with damp extruded particles. The extruded particles are broken into uniform lengths instantaneously and gradually transformed into spherical shapes. In addition, powdered raw materials, which require addition of either liquid or material from a mixer, can be processed in an air-assisted spheronizer.

Spray congealing is a method that is generally used in changing the structure of the materials, to obtain free flowing powders from liquids and to provide pellets ranging in size from about 0.25 mm-2.0 mm. Spray congealing involves allowing a substance of interest to melt, disperse, or dissolve in a hot melt of other additives. The molten mixture is then sprayed into an air chamber wherein the temperature is below the melting point of the formulation components, to provide spherical congealed pellets. The temperature of the cooled air used depends on the freezing point of the product. The particles are held together by solid bonds formed from the congealed melts. Due to the absence of solvent evaporation in most spray congealing processes, the particles are generally non porous and strong, and remain intact upon agitation. The characteristics of the final congealed product depend in part on the properties of the additives used. The feed rate and inlet/outlet temperatures are adjusted to ensure congealing of the atomized liquid droplet. The feed should have adequate viscosity to ensure homogeneity. The conversion of molten feed into powder is a single, continuous step. Proper atomization and a controlled cooling rate are critical to obtain high surface area, uniform and homogeneous congealed pellets. Adjustment of these parameters is readily achieved by one skilled in the art.

The spray congealing method is similar to spray drying, except that solvent is not used. Instead, the active ingredient(s) is dispersed and/or melted into a matrix comprising melt-processable polymer(s). Spray congealing is a uniform and rapid process, and is completed before the product comes in contact with any equipment surface. Most actives and additives that melt without decomposition are suitable for this method.

Conventional spray dryers operating with cool inlet air have been used for spray congealing. Several methods of atomization of molten mass can be employed, such as pressure, or pneumatic or centrifugal atomization. For persons skilled in the spray congealing art, it is well known that several formulation aspects, such as matrix materials, viscosity, and processing factors, such as temperature, atomization and cooling rate affect the quality (morphology, particle size distribution, polymorphism and dissolution characteristics) of spray congealed pellets. The spray congealed particles may be used in tablet granulation form, encapsulation form, or can be incorporated into a liquid suspension form.

Compositions prepared in accordance with certain aspects of the present invention provide amorphous carotenoids that exhibit enhanced solubility and bioavailability without requiring the use of significant amounts of lipids or oils. In fact, certain aspects of the invention relate to compositions containing amorphous carotenoids that are substantially free of lipids, triglycerides, or oils.

Carotenoids produced in accordance with some embodiments of the invention exhibit enhanced stability, solubility and bioavailability even when present in solid state forms such as solid solutions or solid dispersions. The carotenoid may be present in such compositions at levels exceeding about 5% by weight, more particularly exceeding about 10%, and in some cases exceeding about 25%, 40% or even 50% by weight of the composition and still exhibit enhanced solubility and bioavailability compared to crystalline forms of the compound.

Certain polymers function as solubility-enhancing polymers in that the presence of the polymer in the composition improves solubility of the carotenoid under various conditions. The solubility-enhancing polymer provides at least one of the following properties as a result of its presence in the composition compared to a control composition without the solubility-enhancing polymer or to a composition containing the crystalline form of the active:

a) an increase in initial release of at least about 25%, more particularly at least about 100% and in accordance with certain embodiments at least about 200% b) an increase in extent of release of at least about 25%, more particularly at least about 100% and in accordance with certain embodiments at least about 200% c) an increase in maximum plasma concentration of at least about 25%, more particularly at least about 100% and in accordance with certain embodiments at least about 200% d) an increase in $AUC_{0-24h}$ of at least about 25%, more particularly at least about 100% and in accordance with certain embodiments at least about 200%.

Initial release refers to the percent of active released after 15 minutes in accordance with a standard dissolution test method. Extent of release refers to the percent of active released after 240 minutes in accordance with the same standard dissolution test method.

In accordance with particular embodiments of the present invention, a composition prepared from a system comprising a polymer and a carotenoid spray dried from a solvent/non-solvent system as described herein exhibits a dissolution profile wherein the percent active released at some point in time is at least about 25%, more particularly at least about 50% and in certain cases at least about 100% greater than a control composition prepared from a system comprising the same polymer and carotenoid spray dried from the same solvent without the non-solvent. Preferably these limits are obtained within about 120 minutes, more particularly within about 60 minutes and still more particularly within about 30 minutes. Dissolution profiles can be determined using USP apparatus TI (paddles) (VK 7010®, Varian Inc.), with a bath temperature of 37° C. and a paddle speed of 100 rpm for 240 minutes.

In accordance with particular embodiments of the present invention, a composition prepared from a system comprising a polymer and a carotenoid spray dried from a solvent/non-solvent system as described herein exhibits an increase in bulk density or tap density wherein the density is at least about 25%, more particularly at least about 50% and in certain cases at least about 100% greater than a control composition prepared from a system comprising the same polymer and carotenoid spray dried from the same solvent without the non-solvent.

Carotenoid compositions prepared from a solvent/non-solvent system typically result in reduced particle size. In accordance with particular embodiments of the present invention, a composition prepared from a system comprising a polymer and a carotenoid spray dried from a solvent/non-solvent system as described herein results in a reduction of particle size on the order of at least about 50%, more particularly at least about 100% and in certain cases at least about 300% compared to a control composition prepared from a system comprising the same polymer and carotenoid spray dried under similar conditions from the same solvent without the non-solvent.

Compositions of the present invention may be delivered by a wide variety of routes, including, but not limited to: buccal, dermal, intravenous, nasal, oral, pulmonary, rectal, subcutaneous, sublingual, and vaginal. Generally, the oral route is preferred.

Compositions of the invention may be presented in numerous forms. Exemplary presentation forms are powders, granules, and multiparticulates. These forms may be added directly to capsules or may be further compressed to produce tablets, capsules, or pills, or reconstituted by addition of water or other liquids to form a paste, slurry, ointment, suspension or solution. Various additives may be mixed, ground, or granulated with the compositions of this invention to form a material suitable for the above dosage forms.

Compositions of the invention may be formulated in various forms so that they are delivered as a suspension of particles in a liquid vehicle. Such suspensions may be formulated as a liquid or as a paste at the time of manufacture, or they may be formulated as a dry powder with a liquid, typically water, added at a later time but prior to administration. Such powders that are constituted into a suspension are often referred to as sachets or oral powders for constitution (OPC). Such dosage forms can be formulated and reconstituted via any known procedure.

Oral, solid-dose spray dried powders typically have a mean particle size of about 0.5 μm-500 μm and are generally prepared from solutions at concentrations of 1% or more total solids, more particularly from about 2%-50%, and still more particularly from about 3%-30% solids.

Oral, solid dose granules typically have a mean particle size of about 50 μm-5000 μm. Techniques to produce granules include, but are not limited to, wet granulation and various fluid bed granulating methods.

Compositions comprising the carotenoid of enhanced stability, solubility and/or bioavailability described herein may be prepared in accordance with conventional techniques. In accordance with one aspect of the invention, a dosage form is provided comprising carotenoid and a disintegrant. The disintegrant used in the composition is preferably of the so-called superdisintegrant type, disintegrants of this type being well-known to the person skilled in the art. As examples of these disintegrants the following can be mentioned: cross-linked polyvinylpyrrolidones, particularly crospovidone, modified starches, particularly sodium starch glycolate, modified celluloses, particularly croscarmellose sodium (cross-linked sodium carboxymethylcellulose) and LHPC (low-substituted hydroxypropyl cellulose). The disintegrant or superdisintegrant may be present in an amount of from about 2% to about 90%, preferably from about 3% to 60% of the composition.

The carotenoid product produced by these compositions and methods described herein may be administered to man or animal. The compositions described herein may be administered as dietary supplements or as pharmaceutical compositions. The carotenoid composition may be administered in a therapeutically effective amount to a human or animal in need of such treatment. The term "therapeutically effective amount" as used herein refers to an amount of an active ingredient that is effective to treat, prevent or alleviate the symptoms of a disease. The carotenoid compositions of the present invention may be used to treat a variety of diseases. For example, β-carotene may exert an antioxidant effect, and provide immunomodulatory, anticarcinogenic, and anti-atherogenic activity. Lutein and zeaxanthin may provide opthalmoprotective and anticarcinogenic activity, while lycopene may confer anticarcinogenic and antiatherogenic action. These compositions can also be used as a nutrient, a nutritional supplement or a veterinary medicine.

The carotenoid product described herein may be provided in various foods or beverages. Examples of suitable foods include baked goods and non-baked goods, such as nutritional bars, cakes, drink mixes and the like. Examples of beverages include waters, energy drinks, sport drinks, soft drinks, teas and the like.

The carotenoid product described herein may also be provided in a semi-liquid (or semi-solid) form. Examples include, without limitation, ointments, creams, pastes, and salves. These compositions may be administered topically, orally, or sublingually.

The present invention is described in more detail by the following non-limiting example.

EXAMPLE 1

A solution was made containing 50% lutein:50% polyvinylpyrrolidone (Plasdone® K-29/32) from a solvent blend of 33.4% hexanes, 23.3% acetone, 23.3% toluene, and 20.0% dehydrated ethanol. The lutein starting material was a natural blend of lutein, zeaxanthin, and other related carotenoids. The solution contained 2.5% total solids, and was prepared in low-actinic glassware to avoid degrading the lutein.

The solution was spray dried in a darkened room using an SD-Micro® (Niro Inc.) spray dryer. Nitrogen was used for the process and atomization gas to avoid lutein oxidation. A powder product collected in the cyclone jar.

The United States Pharmacopeial HPLC method for the content of total carotenoids confirmed the presence of carotenoids in the spray dried powder.

The crystallinity of the spray dried powder was assessed using DSC (Q1000®, TA Instruments) conducted at 5° C./min heating rate. Compared to the starting crystalline material, the spray dried powder contained the carotenoids in almost entirely amorphous form, as indicated by the essential lack of an endotherm of melting (See the FIGURE).

Changes may be made by persons skilled in the art in the compositions and/or in the steps or the sequence of steps of the method of manufacture described herein without departing from the spirit and scope of the invention as defined in the following claims.

What is claimed is:

1. A composition comprising a solid solution wherein the solid solution comprises one or more carotenoid(s) and one or more solubility-enhancing polymer(s) wherein said carotenoid is substantially amorphous and exhibits enhanced bioavailability compared to a control composition without the solubility-enhancing polymer, and wherein the polymer is selected from the group consisting of polyvinylpyrrolidone, hydroxypropylcellulose, hydroxypropylmethylcellulose, hydroxypropylmethylcellulose acetate succinate, hydroxypropylmethylcellulose phthalate and mixtures thereof.

2. The composition of claim 1 wherein said carotenoid is completely amorphous.

3. The composition of claim 1 wherein the ratio of carotenoid to solubility-enhancing polymer is between about 25% carotenoid: 75% polymer to about 75% carotenoid: 25% polymer.

4. The composition of claim 1 wherein the composition comprises spray dried particles of carotenoid and polymer.

5. The composition of claim 4 wherein the spray dried particles of carotenoid and polymer have an average particle size of from about 0.5 μm-500 μm.

6. The composition of claim 1 wherein the carotenoid comprises a provitamin A carotenoid.

7. The composition of claim 6 wherein the provitamin A carotenoid is selected from the group consisting of α-carotene, β-carotene, β-cryptoxanthin, and mixtures thereof.

8. The composition of claim 1 wherein the carotenoid comprises a non-provitamin A carotenoid.

9. The composition of claim 8 wherein the non-provitamin A carotenoid is selected from the group consisting of lycopene, lutein, zeaxanthin, and mixtures thereof.

10. A dosage form comprising the composition of claim 1.

11. The dosage form of claim 10 wherein the dosage form comprises an oral, solid-dosage form.

12. The dosage form of claim 11 wherein the dosage form provides at least one of:
   a) a maximum plasma concentration for an active form of carotenoid that is at least 1.25 times greater than that of a control composition containing crystalline carotenoid;
   b) an increase in the exposure ($AUC_{0-24h}$) of at least 1.25 times that of a control composition containing crystalline carotenoid.

* * * * *